(12) United States Patent
Hoelzle

(10) Patent No.: US 10,888,428 B2
(45) Date of Patent: Jan. 12, 2021

(54) ADDITIVE MANUFACTURING DEVICE FOR BIOMATERIALS

(71) Applicant: University of Notre Dame du Lac, South Bend, IN (US)

(72) Inventor: David J. Hoelzle, Columbus, OH (US)

(73) Assignee: University of Notre Dame du Lac, South Bend, IN (US)

( * ) Notice: Subject to any disclaimer, the term of this patent is extended or adjusted under 35 U.S.C. 154(b) by 0 days.

(21) Appl. No.: 15/592,789

(22) Filed: May 11, 2017

(65) Prior Publication Data

US 2017/0325932 A1 Nov. 16, 2017

Related U.S. Application Data

(60) Provisional application No. 62/335,438, filed on May 12, 2016.

(51) Int. Cl.
*A61F 2/30* (2006.01)
*B33Y 30/00* (2015.01)
(Continued)

(52) U.S. Cl.
CPC ...... *A61F 2/30756* (2013.01); *A61F 2/30942* (2013.01); *B29C 64/118* (2017.08);
(Continued)

(58) Field of Classification Search
CPC .............. A61F 2/30756; A61F 2/30942; A61F 2/3094; A61F 2240/002;
(Continued)

(56) References Cited

U.S. PATENT DOCUMENTS 5,556,429 A 9/1996 Felt
5,937,951 A * 8/1999 Izuchukwu ........ A61B 17/0684
173/91

(Continued)

FOREIGN PATENT DOCUMENTS

CN 204092271 U 1/2015
WO 2011107599 A1 9/2011
(Continued)

OTHER PUBLICATIONS

Shusterman, Neil H., et al. "Successful use of double-lumen, silicone rubber catheters for permanent hemodialysis access", Kidney International, vol. 35 (1989), pp. 887-890, accessed at kidney-international.org on Nov. 6, 2018. (Year: 1989).*
(Continued)

*Primary Examiner* — Joseph S Del Sole
*Assistant Examiner* — Jamel M Nelson
(74) *Attorney, Agent, or Firm* — Wood Herron & Evans LLP

(57) ABSTRACT

An additive manufacturing (AM) device for biomaterials comprises a reservoir, a shaft, and a material delivery head. The device can be used for intracorporeal additive manufacturing. Material within the reservoir can be expelled by a mechanical transmission element, for example a syringe pump, a peristaltic pump, an air pressure pump, or a hydraulic pressure pump. The reservoir can be a barrel, a cartridge, or a cassette. The reservoir can narrow into the shaft, and the shaft can terminate into the nozzle. The shaft can house an inner tube. The device can have an actuator joint capable of being mechanically linked to a robotic surgical system. The actuator joint can have a motor that drives the mechanical transmission element.

13 Claims, 7 Drawing Sheets

(51) Int. Cl.
*B33Y 10/00* (2015.01)
*B29C 64/118* (2017.01)
*B29C 64/209* (2017.01)
*B29L 31/00* (2006.01)
*A61F 2/08* (2006.01)
*B33Y 80/00* (2015.01)

(52) U.S. Cl.
CPC ............ *B29C 64/209* (2017.08); *B33Y 10/00* (2014.12); *B33Y 30/00* (2014.12); *A61F 2/08* (2013.01); *A61F 2002/0894* (2013.01); *A61F 2002/30962* (2013.01); *A61F 2002/30985* (2013.01); *A61F 2240/002* (2013.01); *B29K 2995/0056* (2013.01); *B29L 2031/7532* (2013.01); *B33Y 80/00* (2014.12)

(58) Field of Classification Search
CPC . A61F 2002/30962; A61F 2002/30985; B33Y 10/00; B33Y 30/00; B33Y 80/00; B29C 64/118; B29C 64/209; B29L 2031/7532
See application file for complete search history.

(56) References Cited

U.S. PATENT DOCUMENTS

| | | | |
|---|---|---|---|
| 6,371,952 B1* | 4/2002 | Madhani | A61B 17/00234 606/1 |
| 6,376,742 B1 | 4/2002 | Zdrahala et al. | |
| 2012/0221011 A1 | 8/2012 | Larkin et al. | |
| 2014/0005661 A1 | 1/2014 | Shelton, IV et al. | |
| 2015/0037445 A1* | 2/2015 | Murphy | C12M 33/00 425/131.1 |
| 2018/0104059 A1* | 4/2018 | Roche | A61K 35/28 |

FOREIGN PATENT DOCUMENTS

| | | |
|---|---|---|
| WO | 2017080646 A1 | 5/2017 |
| WO | 2017184839 A1 | 10/2017 |

OTHER PUBLICATIONS

Biondi, www.Thingiverse.com/thing:539490, 28BYJ-48 Syringe Pump/Paste Extruder, Nov. 11, 2014.

Keriquel, in vivo bioprinting for computer- and robotic-assisted medical intervention: preliminary study in mice, Biofabrication, Mar. 10, 2010, vol. 2, issue 1.

O'Connell, Development of the Biopen: a handheld device for surgical printing of adipose stem cells at a chondral wound site, Biofabrication, Mar. 22, 2016, vol. 8, issue 1.

Cohen, Additive manufacturing for in situ repair of osteochondral defects, Biofabrication, Sep. 8, 2010, vol. 2, issue 3.

Melchels, Additive manufacturing of tissues and organs, Progress in Polymer Science 37, Dec. 8, 2011.

Linda G. Griffith; Emerging Design Principles in Biomaterials and Scaffolds for Tissue Engineering published 2002; Annals of the New York Academy of Sciences; 961:83-95.

Ozbolat et al.; Bioprinting Toward Organ Fabrication: Challenges and Future Trends; published Mar. 2013; IEEE Transactions on Biomedical Engineering; vol. 60. No. 3, pp. 691-699.

Ozbolat et al.; Current Advances and Future Prospectives in Extrusion-based Bioprinting; Available online Oct. 31, 2015; Biomaterials (Elsevier); 76:321-343.

* cited by examiner

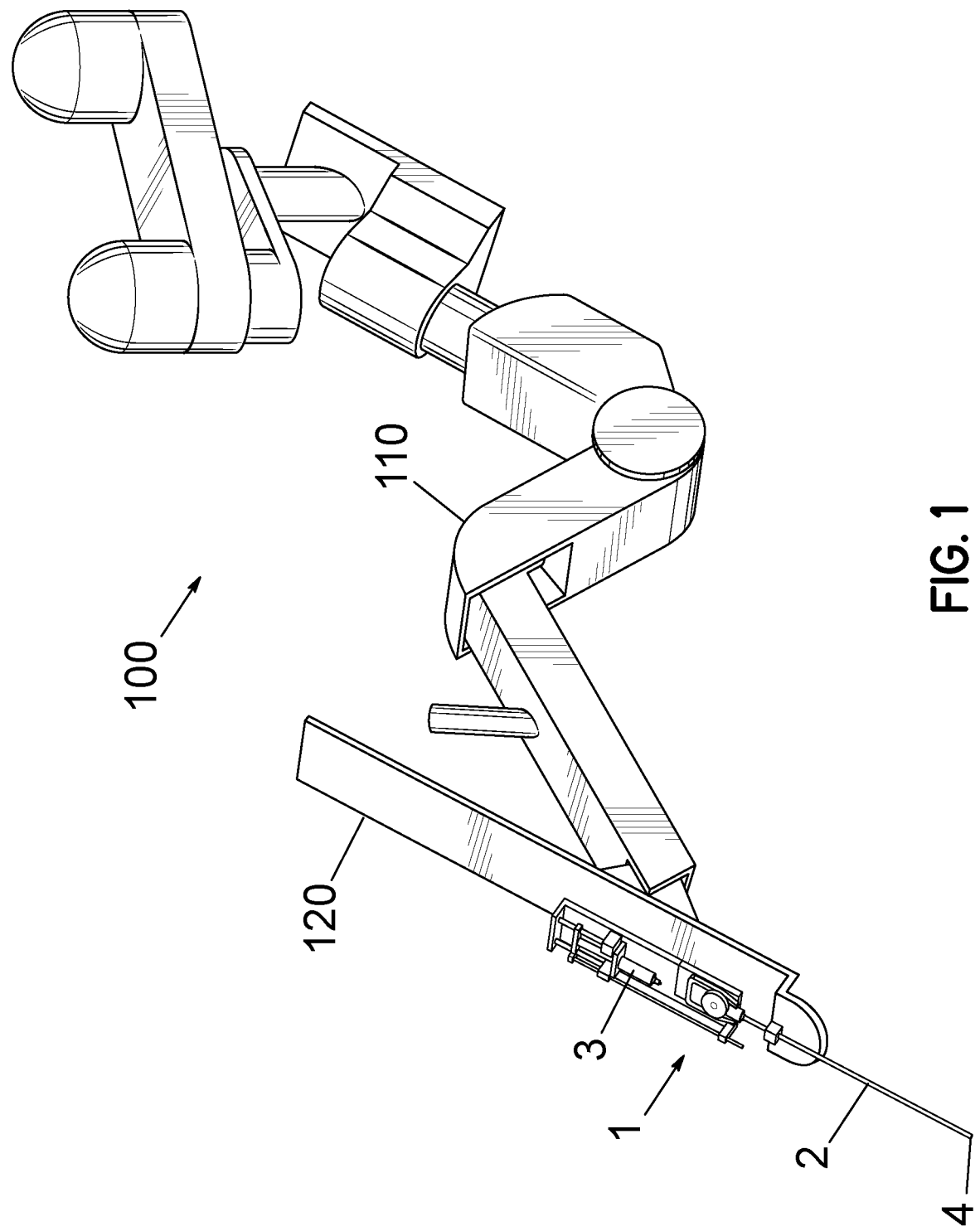

ADDITIVE MANUFACTURING DEVICE FOR BIOMATERIALS

CROSS-REFERENCE TO RELATED APPLICATIONS

This application claims the priority benefit of U.S. Provisional Patent Application No. 62/335,438 filed May 12, 2016, which is hereby incorporated by reference herein as if fully set for in its entirety.

STATEMENT REGARDING FEDERALLY SPONSORED RESEARCH OR DEVELOPMENT

The work described herein was funded, in whole or in part, by grant number CMMI-1552358 from the National Science Foundation. The United States Government has certain rights in the invention.

REFERENCE TO A SEQUENCE LISTING

Not applicable.

BACKGROUND

Field

The present disclosure relates generally to an additive manufacturing device for biomaterials.

Description of Related Art

Medical advancements over the last several decades have yielded two transformative revolutions in medical surgery: robotic endoscopic surgical technologies and synthetic tissue engineering.

Tissue engineering has enabled diseased or damaged tissues to be replaced by artificial scaffolds seeded with the appropriate biologics to restore natural function, all without the limitations of having to harvest tissues. Tangential to the development of tissue engineering has been that of additive manufacturing (AM). AM has enhanced the objectives of tissue engineering to design the correct scaffold materials for form and function and attach the correct biologics to induce de novo growth. The use of ink-jet mechanisms has been used to print precise layers of cells into a matrix of hydrogels. AM has been embraced for its ability to deliver appropriate materials in a construct geometry that is tailored to individual patients. It has been postulated that it might be possible to print whole organs for transplant. While such personalized tissue regeneration has the potential for improved patient outcome, there are always risks of infection and patient morbidity from open surgery.

Endoscopic surgery has enabled surgical operations to be performed through "keyhole" incisions, drastically reducing rates of infection and patient morbidity. The use of robotic endoscopic surgical systems has improved accuracy and precision over handheld endoscopic tools and has furthered this aim.

A shortcoming of additive manufacturing and tissue engineering is that implants are created in a laboratory setting and then transferred to the patient. This often necessitates the use of open surgery. However, there is currently no device for implementing the regenerative medicine techniques described above within the system of the less invasive surgical techniques of robotic endoscopic surgery.

SUMMARY

The shortcomings of above are overcome by an additive manufacturing (AM) device for biomaterials. The device comprises a reservoir, a shaft, and a material delivery head.

The device can be used for intracorporeal additive manufacturing. Material within the reservoir can be expelled by a mechanical transmission element, for example a syringe pump, a peristaltic pump, an air pressure pump, or a hydraulic pressure pump. The reservoir can be a barrel, a cartridge, or a cassette. The reservoir can narrow into the shaft, and the shaft can terminate into the nozzle. The shaft can be between about 250 mm and about 500 mm in length, and between about 5 mm and about 8 mm in diameter. The shaft can house an inner tube. The device can have an actuator joint capable of being mechanically linked to a robotic surgical system. The actuator joint can have a motor that drives the mechanical transmission element.

In another aspect, a method of intracorporeal additive manufacturing is provided. The method comprises providing a supply of biomaterial, providing a biomaterial delivery system including an articulating biomaterial delivery head and a surgical robot mechanically linked to the delivery head, introducing the delivery head into a body cavity, delivering the biomaterial to the delivery head, articulating the delivery head with the robot, and depositing successive layers of the biomaterial to synthesize a three-dimensional object within the body cavity.

The three-dimensional object can be an organ or a portion thereof, tissue, bone, cartilage, ligament, tendon, or muscle.

BRIEF DESCRIPTION OF THE DRAWINGS

The foregoing and other objects, features and advantages of the present technology will be apparent from the following more particular description of various embodiments of the drawings in which like reference characters refer to the same parts throughout the different views. The drawings are not necessarily to scale, emphasis instead being placed upon illustrating the principles of the technology.

FIG. 1 shows a perspective view of an intracorporeal additive manufacturing device integrated with a robotic surgical system.

DETAILED DESCRIPTION

Figure 2A:
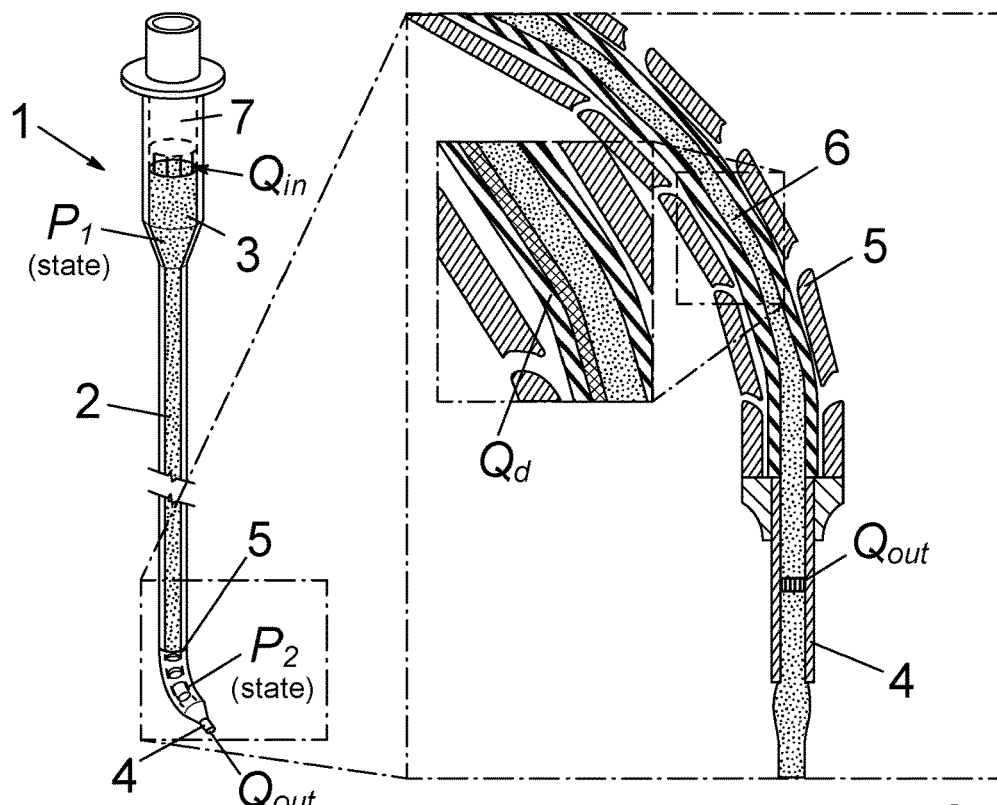
FIG. 2A is a schematic view of a DW endoscopic AM tool and shows the material delivery axis and articulating axes; the inset demonstrates articulation in joint $\theta_{11}$ and coupling between articulation and flow of a YPF.

The present technology provides a device for additive manufacturing of biomaterials. In one embodiment, the device can be used intracorporeally. In yet another embodiment, the device can be utilized during surgery, which can include minimally invasive surgery.

Unless defined otherwise, all technical and scientific terms used herein have the same meaning as commonly understood by one of skill in the art to which the disclosure pertains. Although any methods and materials similar to or equivalent to those described herein can be used in the practice or testing of the present technology, the preferred methods and materials are described herein.

As used herein, the singular forms "a," "an" and "the" are intended to include the plural forms as well, unless the context clearly indicates otherwise.

As used herein, the term "or" has the meaning of both "and" and "or."

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

Tissue Engineering and Additive Manufacturing

As used herein, "tissue engineering" refers to a material or process used to repair or replace portions of tissues or whole tissues, and may particularly refer to repair or replacement of portions of tissues or whole tissues using engineered tissue construtcts. This can include the growth of new connective tissues, or organs, from cells and a scaffold to produce a fully functional organ.

As used herein, the terms "scaffold" or "substrate" or "support", used in the context of tissue production, refer to any surface or structure capable of supporting or providing the environment for growth of cells or tissues. Such supports or substrates have various contemplated surfaces, or are composed of materials, which include, but are not limited to, hydrogels, non-hydrogel polymers, glass, metal, ceramics, and plastic. Such supports and substrates may be naturally derived or artificially derived constructs. Denatured cadaver tissue, engineering materials such as polycaprolactone and Poly-L-lactic-acid, and natural materials such as hydroxyapatite, hydrogels, and collagen are examples of materials that can be used.

As used herein, "additive manufacturing" or "AM" refers to the process of joining materials to synthesize a three-dimensional object by depositing successive layers of a desired material. One non-limiting example is the delivery of a hydrogel microbolus into soft tissue substrates of a body cavity. An additional non-limiting example of AM is the delivery of two dimensional tissue engineered sheets, which can include growth factors or other biologics, via a hydrogel sheet at a location of interest.

As used herein, the terms "hydrogel" or "gel" or "hydrogel matrix" are used interchangeably, and encompass materials including, e.g., poly(hyaluronic acid), poly(sodium alginate), poly(ethylene glycol), diacrylate, chitosan, and poly(vinyl alcohol)-based hydrogels. "Hydrogel" or "gel" is also meant to refer to all other hydrogel compositions disclosed herein, including hydrogels that contain polymers, copolymers, terpolymer, and complexed polymer hydrogels, i.e., hydrogels that contain one, two, three, four or more monomeric or multimeric constituent units. Also used herein, the terms "tissue matrix" or "tissue hydrogel" similarly refer to any composition formed into a porous matrix into which cells or tissue can grow in three dimensions. Hydrogels are typically continuous networks of hydrophilic polymers that are capable of absorbing water.

As used herein, the term "biomaterial" in general refers to a material that is biocompatible, and may be particularly biocompatible for use in tissue engineering as described herein. Such materials can include, but are not limited to, polymer compositions, hydrogels, glasses, metals, ceramics, non-hydrogel polymers, naturally occurring polymers, including collagen and gelatin, and polysaccharides such as glycosaminoglycans. The biomaterial can include an article in different physical forms, such as a membrane, sheet, graft, or mesh. These forms include typical membranes, sheets, grafts, meshes, etc. used in surgery or tissue repair. These articles can include natural products, synthetic products, or combinations thereof. The biomaterial of the present disclosure can be used exclusively to form one of these articles or can be used as a component of one of these articles. "Biomaterial" can be referred to as a "biologic," which refers to a product that may be composed of sugars, proteins, amino acids, or nucleic acids or complex combinations of these substances, or may be living entities such as cells and tissues.

As used herein, the term "organ" refers to a part or structure of the body, which is adapted for a special function or functions, and includes, but is not limited to, the skin, the lungs, the liver, the kidneys, and the bowel, including the stomach and intestines. In particular, it is contemplated that organs which are particularly susceptible to dysfunction and failure arising from an injury are amendable to tissue-engineered reconstruction and are encompassed by the term "organ." "Tissues" are singular or multiply-layered structures, i.e., monolayers or stratified layers of cells, which are organ constituents. One or more different tissues may form an organ or organs. An organ may also be composed of only one type of tissue or cell, or different tissues or cells.

In this description, "cannulas" refer to injection ports, which are typically used to prevent a surgical instrument or guide tube from rubbing on patient tissue. Cannulas may be used for both incisions and natural orifices. For situations in which an instrument or guide tube does not frequently translate or rotate relative to its insertion (longitudinal) axis, a cannula may not be used. For situations that require insufflation, the cannula may include a seal to prevent excess insufflation gas leakage past the instrument or guide tube. For example, for thoracic surgery that does not require insufflation, the cannula seal may be omitted, and if instruments or guide tube insertion axis movement is minimal, then the cannula itself may be omitted. A rigid guide tube may function as a cannula in some configurations for instruments that are inserted relative to the guide tube. Cannulas and guide tubes may be, e.g., steel or extruded plastic. Plastic, which is less expensive than steel, may be suitable for one-time use.

The term "trocar" is used herein to refer generally to an insertion device, which is capable of puncturing an anatomical structure, such as an abdominal wall, to insert a surgical access device, such as a cannula, to aid in performing a surgical procedure.

Robotic Assisted Surgery

As used herein, the term "patient" refers to a human or non-human subject who is being treated, monitored, or the like, for a medical condition, disease or the like, by a healthcare professional.

As used herein, the term "body" refers to the entire structure of a human or non-human subject. The term "body" can also refer to a specific anatomical region of a human or non-human subject.

In a particular embodiment, the device could be utilized as an interchangeable surgical instrument for a robotic surgical system for use in robotic assisted surgery (RAS).

As used herein, "minimally invasive" refers to surgery, such as endoscopic surgery, that can be accomplished without the need to resect tissue in order to gain access to a surgical site. "Minimally invasive" can refer to endoscopy, laparoscopy, arthroscopy, endovascular, keyhole, and like types of surgery. Common to all of these procedures, a surgeon will visualize a worksite within the human body using a camera, and pass surgical instruments through small incisions (or natural orifices) to the worksite. Minimally invasive surgery enables the surgeon to manipulate tissues and organs in a manner which avoids collateral trauma to surroundings tissues, such as would result from open surgery. During such procedures, a surgeon passes instruments through a cannula, manipulates them inside the body through translation and rotation within the cannula, levering the instruments in the body cavity wall and actuating end effectors on the distal end of the instruments. The instruments pivot around centers of rotation, defined by the incision.

As used herein, "robotic assisted surgery" or "RAS" refers to surgery performed through a robotic surgical system. The robotic surgical system can be a telemaniupulation system which allows an operator to manipulate objects from a control operator's computer station. An operator's inputs to control aspects of the minimally invasive surgical instrument assemblies, instruments, and end effectors as described herein are generally accomplished using an intuitive, camera referenced control interface. Generally, the operator's station comprises manual input devices which preferably move with multiple degrees of freedom, and which often further have an actuatable handle for actuating tools. For example, the operator could be a surgeon, who would make a "keyhole" incision in the abdomen using a trocar, inflate the abdomen with $CO_2$ to increase the working and viewing space, and insert a cannula as a portal for placement of other surgical instruments such as placement of actuating tools, such as graspers, scissors, staplers, and the like.

As used herein, "telemanipulation" and like terms generally refer to an operator manipulating a master device (e.g., an input kinematic chain) in a relatively natural way (e.g., a natural hand or finger movement), whereupon the master device movements are made into commands that are processed and transmitted in real time to a slave device (e.g., an output kinematic chain) that reacts nearly instantaneously to the commands and to environmental forces.

During robotic assisted surgery, an operator can manipulate a control device so that a positioning arm of the robotic surgical system can position an intracorporeal additive manufacturing device (1) and lock it in place. The shaft (2) can enter the body through a cannula, which has been inserted through a small incision in a body wall of a patient. The shaft (2) can translate downward, relative to the positioning arm, in response to the operator manipulating the control device. Once inside the body, the operator can position the material delivery head (5) over the desired surgical site. The shaft (2) can articulate about and slide through the cannula, but the neutral axis is at the cannula, limiting flexibility. The operator can manipulate the position of the material delivery head (5) as is required by the particular procedure being performed. Further input by the operator can allow for extrusion of the material within the reservoir (3).

Robotic surgical systems can utilize drive motors and cables for manipulation of instruments. A non-limiting example of a robotic surgical system is described in U.S. Pat. No. 6,371,952. FIG. 1 illustrates an intracorporeal additive manufacturing device (1) coupled to a robotic surgical system (100). The robotic surgical system (100) includes an articulating arm (110) and an end effector, such as a sliding bracket, (120) coupled to the distal end of the articulating arm (110). In this case, the robotic surgical system includes a plurality of actuators, one for each degree-of-freedom (DOF), with each driving one cable of a cable drive system. Cable drive motors are mounted on a sliding bracket (120) and drive respective cables. The actuators are preferably servomotors which are positioned between the intermediate idler pulleys and the proximal idler pulleys. During operation, the sliding bracket is connected to the articulating (110) arm of the robotic surgical system (100). The drive motors operate to move the distal portion of the instrument relative to the sliding bracket. Each drive motor includes a respective encoder for providing rotational position of their respective drive shafts to the operating station computer. In one embodiment, the intracorporeal additive manufacturing device (1) can integrate with such a system, utilizing a drive motor to activate the plunger (7) through a mechanical transmission element, controllably expelling the material in the reservoir (3).

As used herein, the term "mechanical transmission element" can refer to any geared mechanism or friction drive system that is capable of providing controlled application of power. In one non-limiting embodiment of the device, the mechanical transmission element could include a rack and pinion system to control the plunger (7) and expel material from the reservoir (3). In another non-limiting embodiment, the mechanical transmission element could include a cable (10) and pulley (11). While an embodiment described herein uses the motors on the RAS instrument to drive the interchangeable tool, extra motors could be mounted into the interchangeable tool itself.

Figure 5:
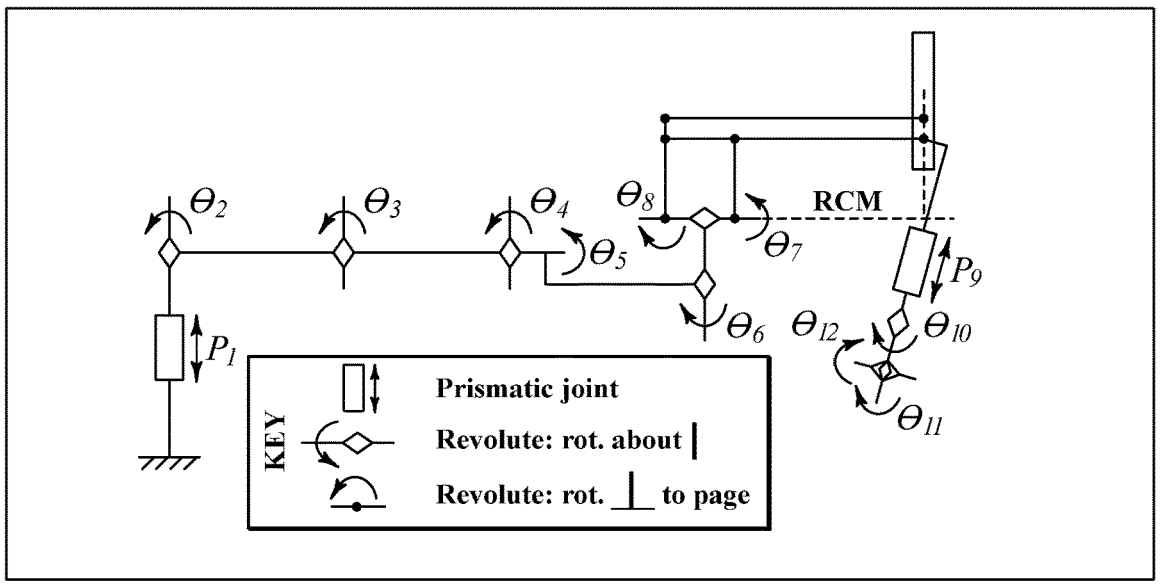
FIG. 5 is a diagram illustrating a kinematic chain of a robotic surgical system. Joints 1-6 are fixed during a surgery and 7-12 provide the six DOFs.

The kinematics of such robotic surgical systems are well characterized (Sun et al. 2007; Trejos and Patel 2005; King et al., 2012, Lum et al. 2006). As described in a non-limiting example (U.S. Pat. No. 6,371,952) joints $P_1$ and revolute joints $\theta_2$ through $\theta_6$ are fixed during operation and are only to establish a position (FIG. 5). Once fixed, revolute joint $\theta_7$ defines pitch, revolute joint $\theta_8$ defines yaw, and prismatic joint $P_9$ defines translational axes; the design is such that a remote center of motion (RCM) is maintained at the trocar as to not stress the incision. Distal to $P_9$ is an interchangeable RAS tool, such as the present technology, an intracorporeal additive manufacturing device (1) that has at least three revolute joints: $\theta_{10}$ defines roll, $\theta_{11}$ defines pitch, and $\theta_{12}$ defines yaw, depending on function, providing an intracorporeal roll, pitch, and yaw. In total there are six DOFs. Joints $\theta_1$-$P_9$ are driven by permanent geared motors and linkages and joints $\theta_{10}$-$\theta_{12}$ are driven by permanent motors and an attached interchangeable tool (1) that has cable transmission assemblies to transfer work along the tool. This is just one example of a robotic surgical system with which the present technology could function as an interchangeable tool for and is used for illustrative purposes only as a non-limiting example. One skilled in the art can appreciate that the present technology could function as an interchangeable tool in a robotic surgical system with a different kinematic organization.

Additive Manufacturing Instrument

Referring to FIG. 1, in a particular embodiment, the intracorporeal additive manufacturing device, shown generally by (1), is a slender tool with a shaft (2) having a diameter of about 8 mm and a length of about 500 mm, a reservoir (3), an articulating delivery head (5) which positions a nozzle (4).

Referring to FIG. 2A, the shaft (2) has a distal end which is an articulating material delivery head (5). The articulating material delivery head (5) comprises three joints which provide articulating axes, $\theta_{10}$ defines roll, $\theta_{11}$ defines pitch, and $\theta_{12}$ defines yaw. The shaft (2) can contain an inner tube (6) that winds through the shaft (2) and nozzle (4), transmitting material out through the nozzle (4). Alternatively, the shaft (2) could have an external tube to deliver material, or the shaft (2) could just be hollow, being both the tube for delivering the material and the structure. A plunger (7) transmits extrusion pressure through the entire reservoir (3) of material. The plunger is driven by a mechanical transmission element.

Figure 3:
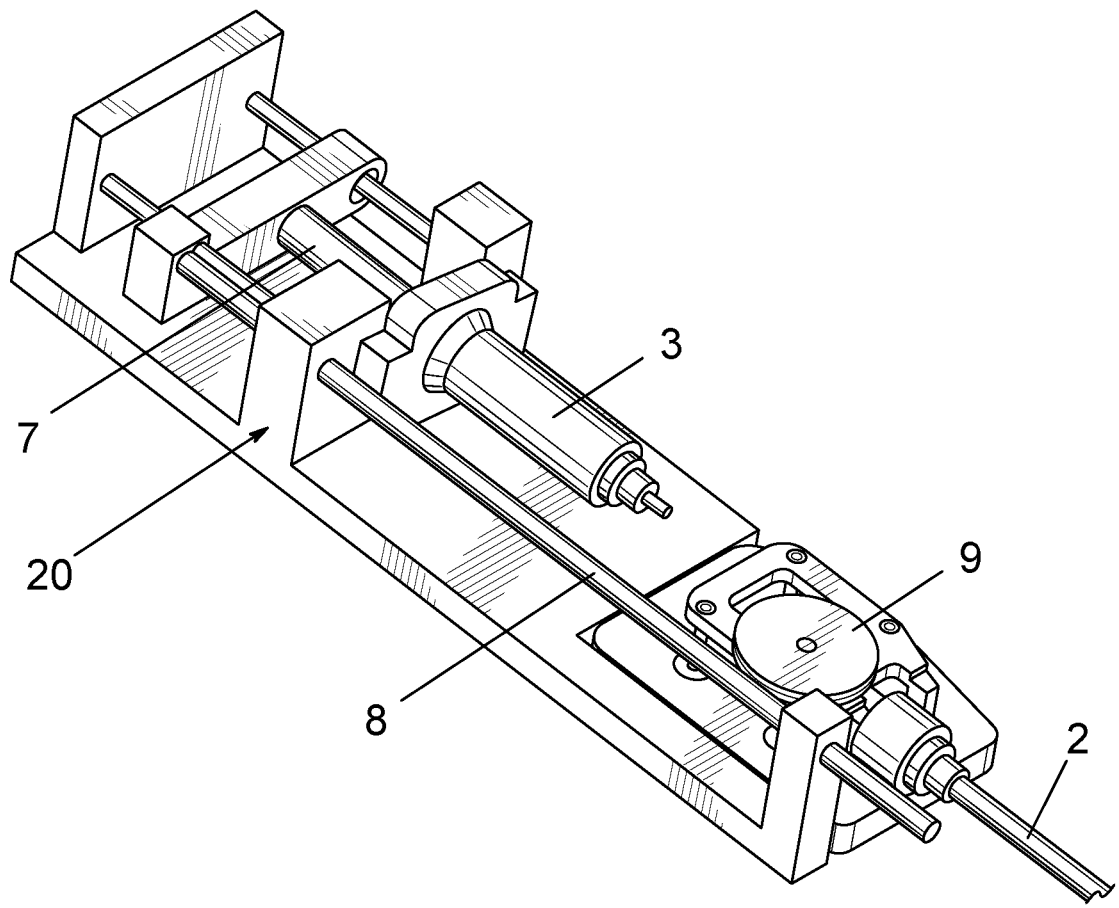
FIG. 3 is a perspective view of one embodiment of an intracorporeal additive manufacturing device wherein a rack and piston system drives a plunger to extrude material from a reservoir.

Referring to FIG. 3, there is illustrated one example of an intracorporeal additive manufacturing device (1) having a frame or chassis (20) and wherein the mechanical transmission elements include a rack (8) and pinion (9) system to drive the plunger (7), transmitting extrusion pressure through the reservoir (3) such that material is expelled from the reservoir (3) into the shaft (2).

Figure 4A:
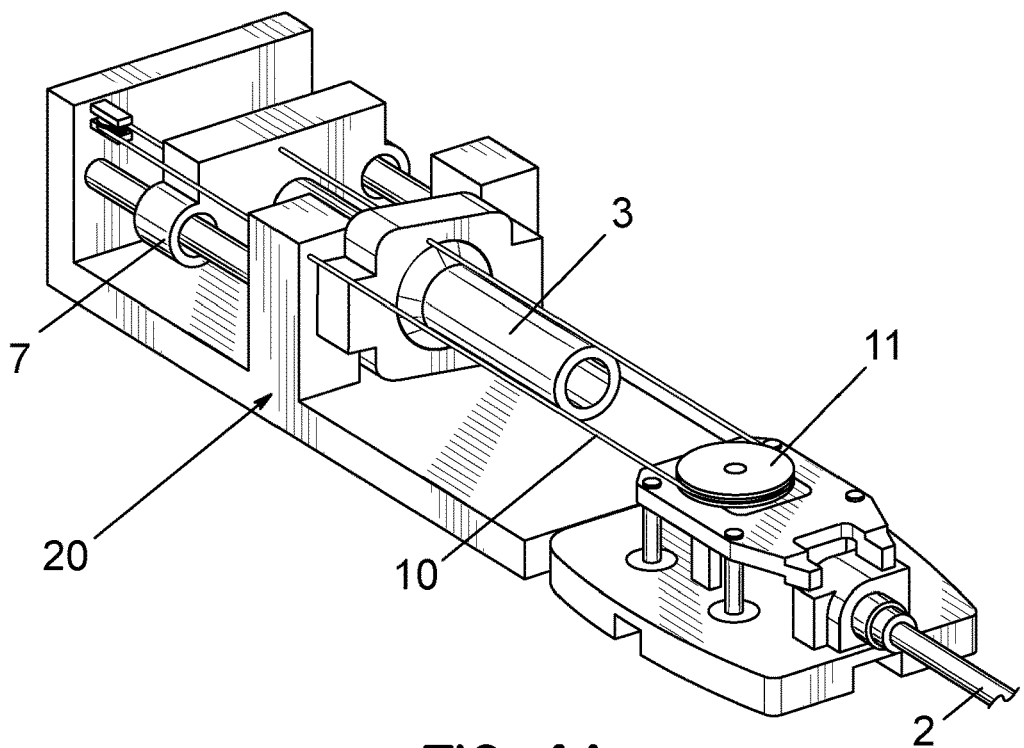
FIG. 4A is a perspective view of one embodiment of an intracorporeal additive manufacturing device wherein a cable driven system drives a plunger to extrude material from a reservoir.
Figure 4B:
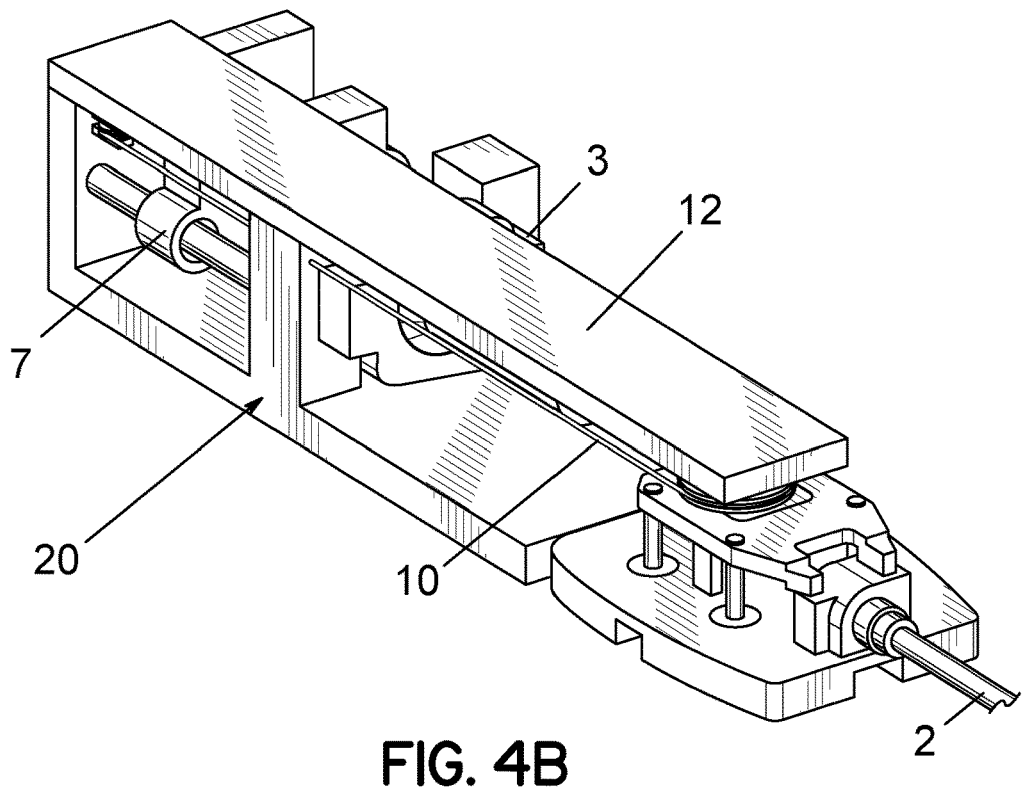
FIG. 4B is a view similar to FIG. 4A and shows a protective cover holding the cable taut and the pulley in place.

Referring to FIG. 4A, in an alternative embodiment, the plunger of the intracorporeal additive manufacturing device could be driven by a cable (10) and pulley (11) system. FIG. 4B shows this particular embodiment with a cover (12) to keep the pulley (11) attached and the cable (10) taut.

EXAMPLES

The technology will be more fully understood upon consideration of the following non-limiting examples, which are offered for purposes of illustration, not limitation.

Example 1: Determining Direct Write Printing for Endoscopic AM Modality

The intracorporeal environment presents interesting challenges for material accumulation at a soft tissue site. A successful intracorporeal AM tool can: directly deliver material as opposed to using a particle or liquid bed that would be impossible to remove from the body, operate at physiological temperatures, not need an unobstructed optical path, have the potential to be configured in a slender form factor to fit through a trocar, be able to fabricate simple structures in a clinically relevant operation room (OR) time of less than two hours, and have quick setting materials available. Room temperature direct write (DW) printing (also termed micro-extrusion, robocasting, or micro-robotic deposition) satisfies these needs (Table 1).

Furthermore, in DW the print head has intimate contact with the substrate, enabling the potential use of a sharpened nozzle to pierce the native tissue and extrude material abutments as the base layer. The extruded filaments can span structural gaps and thus porosity on the order of 50-400 µm is easily built. Biocompatible hydrogels with embedded growth factors and cells are a material option.

TABLE 1

Space of endoscopic AM needs and candidate AM tools demonstrating that direct write printing satisfies the needs

| | AM Tools | | | | | | | | | |
|---|---|---|---|---|---|---|---|---|---|---|
| Needs | direct write | polyjet | fused dep. modeling | stereo lithography | selective laser sinter. | projection lithography | direct metal laser sintering | laser metal deposition | binder printing | lam. object manufact. |
| Direct material delivery | X | X | X | | | | | X | | X |
| Physiological temperatures | X | X | | X | | X | | | X | X |
| Optics free | X | | X | | | | | | X | X |
| Slender form factor possible | X | X | X | X | X | X | X | | X | |
| Less than 2 hrs OR time | X | X | X | X | X | X | X | X | X | X |
| Quick setting materials | X | X | X | X | X | X | X | X | X | X |

Example 2: Fundamental Manufacturing Limitations of an Endoscopic AM Tool

Figure 6A:
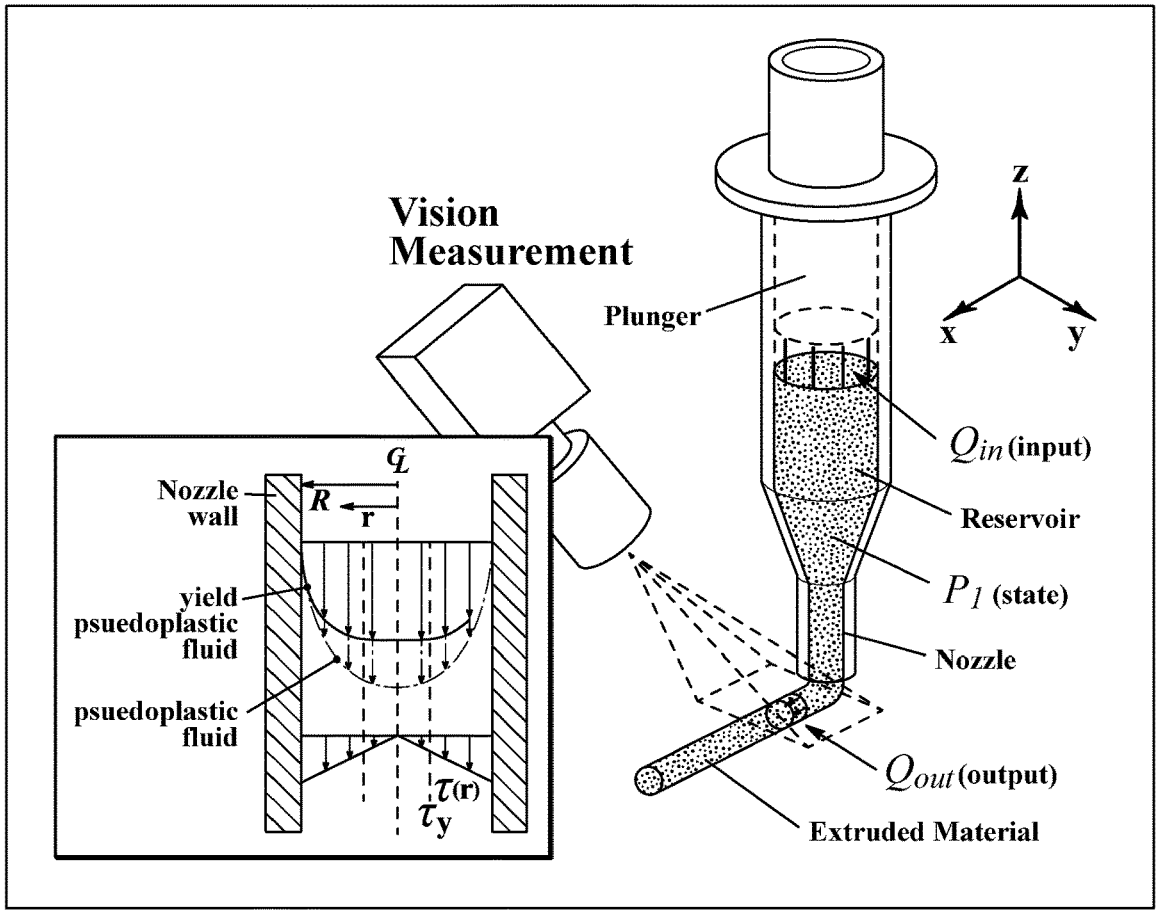
FIG. 6A is a schematic perspective view of microextrusion in DW detailing input and output variables and system states.
Figure 6B:
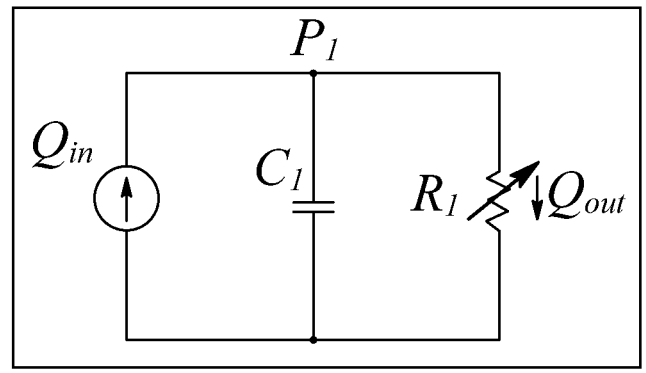
FIG. 6B shows that microextrusion can be modeled as a RC circuit with a nonlinear resistor.

Although the DW AM modality is an appropriate tool for intracorporeal AM, the fluid mechanics of DW challenge the accurate delivery of material. In general, other AM tools only interact with (e.g. crosslink, sinter, melt, spray) the minute amount of material that is currently being added. In contrast, the plunger in DW transmits the extrusion pressure through the entire reservoir of material (FIG. 6A). The large volume being acted on has a large fluidic capacitance and thereby makes the accurate delivery of material considerably more challenging; pressure is stored in the compliance in the fluid and vessel walls, acting as a capacitor. A simple experiment demonstrates the repercussions of large fluidic capacitances (FIG. 6C); material can be accurately metered in steady-state, however transient such as starting or stopping of flow are not easily controlled.

The model between the microextrusion input, plunger displacement rate $Q_{in}(t)$, and the output, volumetric flowrate of extruded material $Q_{out}(t)$, is determined by the fluid properties and microextruder geometry. Many build materials in DW are characteristic of yield-pseudoplastic fluids (YPFs): YPFs have a critical yield stress, $\tau_y$, at which material will not deform for a shear stress $\tau$ less than $\tau_y$, and are shearthinning, meaning that the viscosity decreases with increasing shear rate. The model of YPF flow can be coupled into a complete model of extrusion in DW, modeled as a simple resistor-capacitor (RC) circuit where the nonlinear resistor captures the model of a YPF through a constricted nozzle and the capacitor $C_1$ captures the effective capacitance of a compressible material in a vessel with flexible walls. The dynamic input and output relationship is given by the scalar state equation in reservoir pressure, $P_1(t)$, $\chi$ is a scalar that captures geometric and material properties and the nonlinear function $f_1(P_1(t))$ captures the piecewise continuous model that describes nozzle flow of a YPF.

$$\frac{dP_1(t)}{dt} = \chi(f_1(P_1(t)) - Q_{in}(t)) \quad \text{EQUATION 1}$$

$$Q_{out}(t) = f_1(P_1(t))$$

Figure 6C:
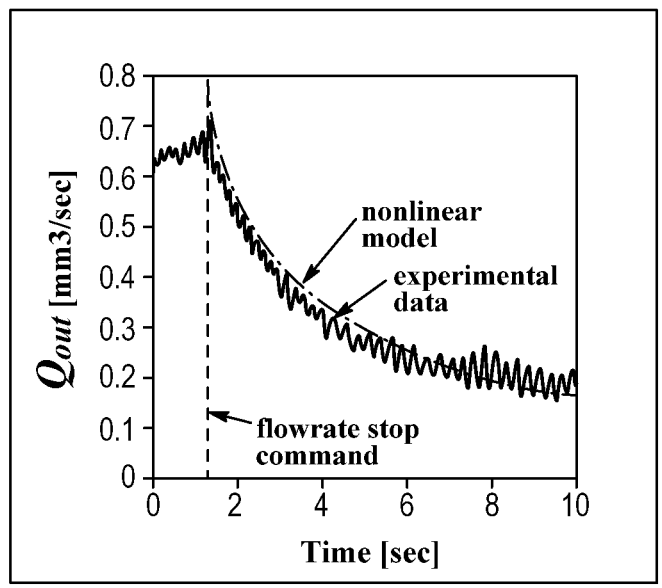
FIG. 6C shows that the nonlinear RC circuit model captures the dominant dynamics, as measured by machine vision.

Equation 1 has been validated experimentally (FIG. 6C). Furthermore, a laboratory-grade DW system can be integrated with a suite of sensors and an advanced control algorithm to accurately control material delivery rates. These tools have been used to fabricate hydroxyapatite (HA) scaffolds with multiple domains of different material microstructures, spatially graded macro-structures, and near net-shape form factors.

Figure 2B:
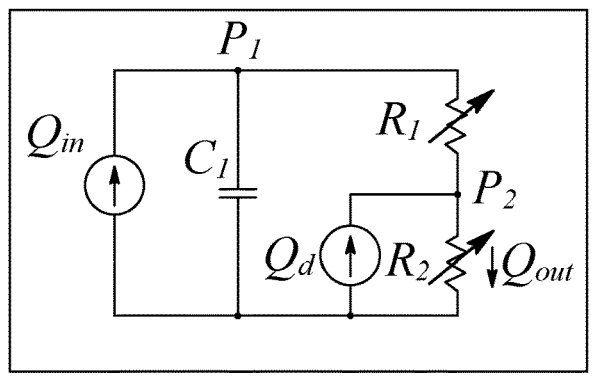
FIG. 2B shows a circuit model of an intracorporeal AM tool.
Figure 2C:
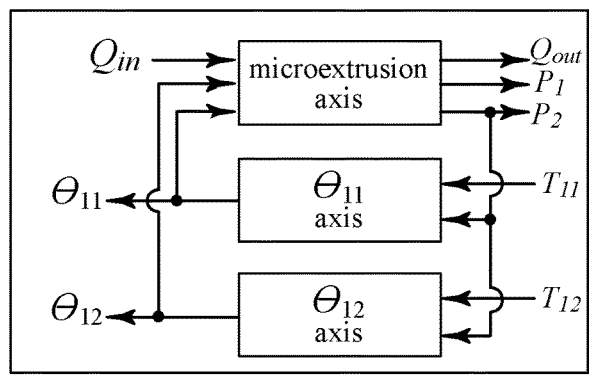
FIG. 2C shows coupling between positioning axes and microextrusion axis.

An endoscopic AM tool will not be optimally configured like a commercial DW tool. Scalar $\chi$ is proportional to the effective bulk modulus of the fluid—a function of the fluid itself and compliance in the walls of the reservoir and channel—and proportional to channel radius to the negative third power. With the transition from the standard, rigid microextrusion systems used in DW to the long, slender tools that must be used in endoscopic AM (FIG. 2), there will be both an increase in fluid line capacitance and fluidic resistance and therefore poorer dynamic coupling between the input and output. Furthermore, the fluid delivery subsystem is not independent of the positioning subsystem as it is in a laboratory DW. These interactions are best understood by considering each subsystem as their own axis. The fluid delivery axis winds through the articulating positioning axes, which bends with articulation ($\theta_{11}$ and $\theta_{12}$ in FIG. 5) and thus drives fluid flow by squeezing the control volume ($Q_d$ in FIG. 2). Likewise, the pressurized fluid delivery axis imposes a force on the positioning axes, $\theta_{11}$ and $\theta_{12}$, acting as a force disturbance as pressure is modulated to control materials delivery. An intracorporeal AM tool is thus a coupled MIMO (multiple input, multiple output) system (FIG. 2c).

Example 3: The Dynamics of Microextrusion of a YPF in Laminar Flow in an Endoscopic AM Tool Equation 1 with a single input, state, and output expands to the two-dimensional state equation (the time argument t has been omitted for brevity of notation), where the nonlinear, piecewise-continuous functions $f_1$, $f_2$, and $f_3$ are a function of YPF properties and intracorporeal AM tool geometry and $Q_d$ is a disturbance flow driven by channel deformation.

$$\frac{d}{dt}\begin{bmatrix}P_1 \\ P_2\end{bmatrix} = \begin{bmatrix}f_1(P_1, P_2, Q_{in}) \\ f_2(P_1, P_2, Q_d)\end{bmatrix} \quad \text{EQUATION 2}$$

$$Q_{out} = f_3(P_2),$$

A general, parametric model of these functions will be synthesized to better understand the implications of tool geometry and material choice on the ability to precisely meter fluid flow.

Example 4: Coupling Dynamics of Parallel Kinematic Articulating Manipulators with a Central Fluid Line Under High Pressure Whereas Equation 2 considers the simplified case where channel wall deformation driven flow, $Q_d$, is represented as an independent input: $Q_d$ is in fact a function of articulation velocity: $Q_d = f(\dot{\theta}_{11}, \dot{\theta}_{12})$. Furthermore, articulation angles $\theta_{11}$ and $\theta_{12}$ are driven by cable tension, $T_{11}$ and $T_{12}$; intra-channel pressures will exert a disturbance force on the articulating actuators. Taken together, the dynamics of an endoscopic AM tool are described by a nonlinear MIMO model (Equation 3) where $A(x)$, $B(u)$, and $C(x)$ are nonlinear functions of the states, x, and inputs, u, and are currently not known. y is a vector of outputs. Equation 3 will discover scientific knowledge of the compiled dynamics that couples different axes in an endoscopic AM tool (FIG. 2C).

$$dx/dt = A(x) + B(u)$$

$$y = C(x)$$

$$x = [P_1, P_2, \theta_{11}, \dot{\theta}_{11}, \theta_{12}, \dot{\theta}_{12}]^T; u = [Q_{in}, T_{11}, T_{12}]^T; y = [Q_{out}, \theta_{11}, \theta_{12}]^T \quad \text{EQUATION 3:}$$

Example 5: Multi-Physics Computational Models of a YPF Fluid Interacting with Compliant Actuators The parametric Equation 3 will be complex and therefore simplifying assumptions, such as assuming the fluid to be pseudoplastic ($\tau_y = 0$) or Newtonian, will have to be employed to extract a tractable model. Hence understanding of this comprehensive parametric model will be augmented using multiphysics simulations that capture the complete physical description of a YPF. Operating points of interest, such as imposing a pressure step at a flexed position in a single articulation axis or flexing a single articulation axis at a steady pressure $P_2$, will be simulated. The multiphysics tool COMSOL® will be used.

Example 6: Two-DOF Micro-Extrusion Actuator

Figure 7A:
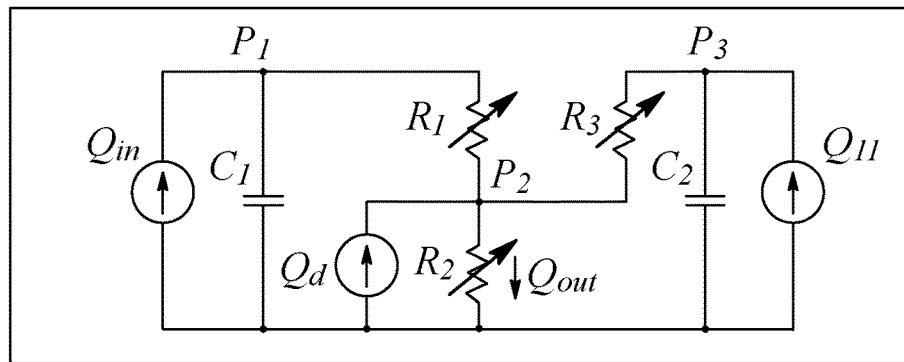
FIG. 7A shows a circuit model of a DW tool augmented with a short-stroke pump, Qss.
Figure 7B:
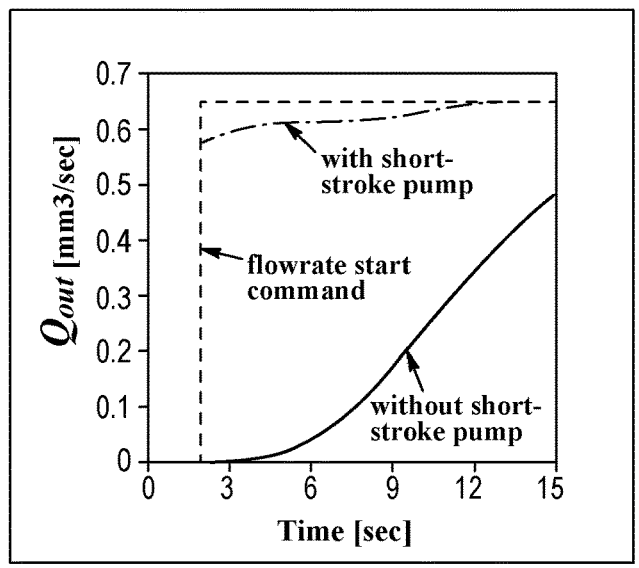
FIG. 7B shows simulation results predict that input Qss will be tightly coupled to the output Qout.

The transients in desired extrusion rates are difficult to control and thus challenge accurate scaffold manufacture using DW. Advanced learning-based control algorithms that are robust to batch-to-batch materials variations (Hoelzle et al., 2011) have been successfully used, however these methods require machine learning and are thus not appropriate for the surgical theatre. If the fluid delivery capacitance could be significantly decreased, better dynamic input/output coupling could be achieved, hence better control of material delivery during transients. There are two feasible methods as to which the system capacitance can be significantly decreased: 1) significantly decrease the microextruder volume at the expense of maximum attainable structure size; or 2) only interface with the material at the nozzle outlet. Method 2 will be pursued, interfacing with the material at the nozzle outlet, and the hypothesis that a two-DOF actuator that decouples the fluidic capacitance from the flowrate output will reduce the rise time of the flowrate response by a statistically significant margin will be tested. The standard DW system with a single plunger driven pump can be reconfigured to include a small short-stroke pump, $Q_{ss}$, that drives a minute amount of material at the nozzle outlet (FIG. 7). In comparison to the nominal system, the dynamics between the short-stroke pump and the output, $Q_{out}$, have been decoupled from the reservoir capacitance by the large, non-linear resistor separating the pump and syringe reservoir. Simulation results using an idealized short-stoke pump ($C_2=0$) and a pseudoplastic fluid ($\tau_y=0$) demonstrate a difference in rise time greater than a factor of five (FIG. 7B).

The two-DOF extrusion architecture complicates the model. An electric circuit analogy for the fluidic network is shown in FIG. 7A. The short-stroke pump has a circuit architecture that is similar to a standard microextruder; however, water is used as the transmission medium, hence Newtonian flow, and the dead volume can be made very small because the short-stroke pump volume is small, hence $C_2 \ll C_1$. The fundamental knowledge gained in this subtask will enable one to predict performance for an endoscopic AM tool and theoretically compare competing flowrate control strategies.

Figure 8:
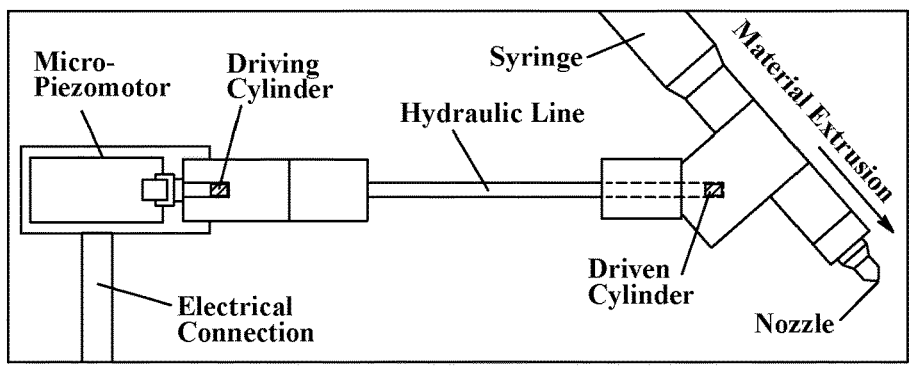
FIG. 8 shows a design and prototype of a short-stroke pump.

Modeling results in will be empirically validated. A DW tool with a custom multimaterial DW head, a machine vision system, a custom control system, and an established materials system (FIG. 8) will be used to quantify output 5% rise time over a range of operating parameters, build material characteristics, and desired flowrates. Rise time will be computed from the flowrate response measured by machine vision, as previously employed (Hoelzle et al. 2011). Statistical significance will be assessed using student's t-test if the data distribution is normal or using data transform and nonparametric methods for non-normal data. To complement the hypothesis test, model predictivity for the nominal DW model, Equation 1, and the DW model augmented with a short-stroke pump will be quantified. Output predictivity will be quantified by the root mean square of the error between the actual measured $Q_{out}$ and the predicted $Q_{out}$. Stochasticity will be quantified by the root mean square difference amongst repetitions of trials.

By decoupling output $Q_{out}$ from the reservoir capacitance $C_1$ and the input $Q_{in}$, pressure $P_2$ will be able to be better modulated and hence start and stop material more accurately and therefore more accurately meter material intracorporeally.

Example 7: Dynamics and Control of the MIMO Endoscopic AM System

Equation 3 captures the dynamic coupling between material extrusion axes and positioning axes $\theta_{11}$ and $\theta_{12}$; however, the model is blind to the pose of the nozzle in 3D space. Ultimately, the nozzle in an endoscopic AM tool will have to track complex, contoured pose trajectories in time and for this all elements of the kinematic chain from $\theta1$ to $\theta_{12}$ (FIG. 5) must be understood. The kinematics of RAS systems are complex, but well-understood. Researchers typically assume quasi-static dynamics and hence inertial and viscous effects are ignored. The kinematic chain is thus described by a sequence of nonlinear transformation matrices that concatenates serial joint positions to define end effector pose, Equation 4.

$$T_{12}^{0}=T_{1}^{0}T_{2}^{1} \ldots T_{12}^{11};\qquad \text{EQUATION 4:}$$

Inverse kinematic synthesis tools are then used to prescribe individual joint trajectories to achieve a desired end effector pose. Equation 4 uses the standard Denavit-Hartenberg convention; each $T_i^{i-1}$ is the 4×4 matrix that defines the change in pose from each link, from i−1 to i, and $T^0{}_{12}$ defines the pose of link 12 in reference to the base link, link 0. These quasi-static relationships, however, do not include the time derivatives of $\theta_{11}$ and $\theta_{12}$ which each drive local fluid flows in dynamic Equation 3. For real-time, efficient computation of joint motions, a theoretical framework that integrates quasi-static and dynamic motions will be defined to better understand endoscopic AM motion and materials delivery.

The device will be built through the integration of a partial RAS design (only joints $\theta_7$-$\theta_{12}$) with an integrated fluid delivery subsystem that is optimized given from the aforementioned Equations 1, 2, and 3. A case prognosis and surgical intervention will be defined for testing the precise injection of micro-boluses and fabrication of conformal sheets. The case surgery will define a mock-up of the pelvic cavity as a model cavity for testing.

Example 8: Synthesize a MIMO Control Systems for Endoscopic AM

The knowledge gained in the previous examples provides the understanding required to control each joint angle and extrusion input to fabricate simple structures inside a biological mock-up. The MIMO control of such a nonlinear system requires and understanding of the nonlinear models and the implications of linearizing the models for control when the different axes evolve on different time scales—positioning axes will have a time constant that is an order of magnitude faster than the extrusion axes. Synthesized MIMO control laws will be evaluated in simulation and in the fabrication of simple planar constructs on the cavity surfaces of the biological mock-up. A machine vision system, an approximation of a video endoscope, will be used to evaluate manufacturing accuracy. Measured volumetric flowrate will be compared to reference flowrates. Final construct architecture will be characterized using micro-computed tomography for digital correlation to idealized construct geometries to quantify fabrication error using the 3D spatial 2-norm of the error. The materials system will be HA colloidal ink.

The various embodiments of the invention shown and described are merely for illustrative purposes only, as the drawings and the description are not intended to restrict or limit in any way the scope of the claims. Those skilled in the art will appreciate various changes, modifications, and improvements which can be made to the invention without departing from the spirit or scope thereof. For example, the device could be used for the insertion of radiopaque marker particles to mark a region for followup imaging, and used for adding radioactive particles for brachytherapy. The invention in its broader aspects is therefore not limited to the specific details and representative apparatus and methods shown and described. The invention resides in each individual feature described herein, alone, and in all combinations of any and all of those features. Departures may therefore be made from such details without departing from the spirit or scope of the general inventive concept. Accordingly, the scope of the invention shall be limited only by the following claims and their equivalents.

What is claimed is:

1. A biomaterial delivery system for printing a tissue engineering construct inside a patient's body, the biomaterial delivery system comprising:
   a robotic surgical system having an articulating arm and an end effector coupled to a distal end of the articulating arm, the end effector configured to have at least three degrees of movement being controlled by the robotic surgical system; and
   an additive manufacturing device comprising:
      a frame releasably mounted to the end effector;
      a first mechanical transmission element operatively connected to the frame and engaged with the end effector so that the end effector may control the operation of the first mechanical transmission element;
      a biomaterial reservoir selectively removably connected to the frame, the biomaterial reservoir adapted to hold biomaterial;
      a syringe pump capable of generating pressure in the reservoir, the syringe pump operatively coupled to the first mechanical transmission element so that biomaterial may be expelled from the biomaterial reservoir when the first mechanical transmission element is operated by the end effector;
      a shaft operatively connected to a discharge end of the biomaterial reservoir, the shaft adapted to transport biomaterial therethrough, the shaft configured to be at least partially inserted into a patient's body; and
      a nozzle operatively connected to a discharge end of the shaft, the nozzle configured to be inserted into the patient's body and discharge biomaterial therein;
      wherein the nozzle is operatively coupled to the end effector such that, on command of the robotic surgery system, the end effector moves the nozzle while depositing biomaterial to print a tissue engineering construct inside the patient's body.

2. The biomaterial delivery system of claim 1, wherein the additive manufacturing device further comprising:
   an articulating joint having at least one degree of freedom of movement, the articulating joint being operatively connected to a distal end of the shaft and configured to move the nozzle along the at least one degree of freedom of movement of the articulating joint;
   a second mechanical transmission element operatively coupled to the articulating joint and engaged with the end effector so as to move the nozzle corresponding to the at least one degree of freedom of movement of the articulating joint; and
   wherein, on command of the robotic surgery system, the end effector moves the nozzle corresponding to the at least one degree of freedom of movement of the articulating joint.

3. The biomaterial delivery system of claim 2, wherein a discharge end of the nozzle being sharpened to pierce tissue and deliver biomaterial inside the tissue.

4. The biomaterial delivery system of claim 1, wherein a discharge end of the nozzle being sharpened to pierce tissue and deliver biomaterial inside the tissue.

5. The biomaterial delivery system of claim 1, the additive manufacturing device further comprising a tube disposed next to the shaft and the shaft can be either hollow or not hollow.

6. The biomaterial delivery system of claim 5, wherein the tube is disposed inside the shaft.

7. The biomaterial delivery system of claim 1, wherein the frame further includes a slidable rack operatively coupled to the syringe pump and the first mechanical transmission element includes a pinion configured to engage the rack and thereby move the rack when the pinion rotates.

8. The biomaterial delivery system of claim 1, wherein the frame further includes a cable operatively coupled to the syringe pump and the first mechanical transmission element includes a pulley configured to engage the cable and thereby move the cable when the pulley rotates.

9. A biomaterial delivery system for printing a tissue engineering construct inside a patient's body, the biomaterial delivery system comprising:
   a robotic surgical system having an articulating arm and an end effector coupled to a distal end of the articulating arm, the end effector configured to have at least three degrees of movement being controlled by the robotic surgical system; and
   an additive manufacturing device comprising:
      a frame releasably mounted to the end effector;
      first mechanical transmission element operatively connected to the frame and engaged with the end effector so that the end effector may control the operation of the first mechanical transmission element;
      a biomaterial reservoir selectively removably connected to the frame, the biomaterial reservoir adapted to hold biomaterial;
      a syringe pump capable of generating pressure in the reservoir, the syringe pump operatively coupled to the first mechanical transmission element so that biomaterial may be expelled from the biomaterial reservoir when the first mechanical transmission element is operated by the end effector;
      a shaft operatively connected to a discharge end of the reservoir;
      a nozzle operatively connected to a discharge end of the shaft, the nozzle adapted to direct a flow of biomaterial being discharged from the nozzle; and
      a tube disposed within the shaft, the tube configured to transport biomaterial between the biomaterial reservoir and the nozzle;
      wherein the nozzle is operatively coupled to the end effector such that, on command of the robotic surgery system, the end effector moves the nozzle while depositing biomaterial to print a tissue engineering construct inside the patient's body.

10. The biomaterial delivery system of claim 9, wherein the additive manufacturing device further comprising:
    an articulating joint having at least one degree of freedom of movement, the joint being operatively connected to a distal end of the shaft and configured to move the nozzle along the at least one degree of freedom of movement of the articulating joint;
    a second mechanical transmission element operatively coupled to the articulating joint and engaged with the end effector so as to move the nozzle corresponding to at least one degree of freedom of movement of the articulating joint; and
    wherein, on command of the robotic surgery system, the end effector moves the nozzle corresponding to the at least one degree of freedom of movement of the articulating joint.

11. The biomaterial delivery system of claim 9, wherein a discharge end of the nozzle being sharpened to pierce tissue and deliver biomaterial inside the tissue.

12. A biomaterial delivery system for printing a tissue engineering construct inside a patient's body, the biomaterial delivery system comprising:
- a robotic surgical system having an articulating arm and an end effector coupled to a distal end of the articulating arm, the end effector configured to have at least three degrees of movement being controlled by the robotic surgical system; and an additive manufacturing device comprising:
- a frame releasably mounted to the end effector;
- a first mechanical transmission element operatively connected to the frame and engaged with the end effector so that the end effector may control the operation of the first mechanical transmission element;
- a biomaterial reservoir selectively removably connected to the frame, the biomaterial reservoir adapted to hold biomaterial;
- a syringe pump capable of generating pressure in the reservoir, the syringe pump operatively coupled to the first mechanical transmission element so that biomaterial may be expelled from the biomaterial reservoir when the first mechanical transmission element is operated by the end effector;
- a shaft operatively connected to a discharge end of the biomaterial reservoir, the shaft configured to be at least partially inserted into a patient's body;
- a nozzle operatively connected to a discharge end of the shaft, the nozzle configured to be inserted into the patient's body and discharge biomaterial therein;
- an articulating joint having at least one degree of freedom of movement, the articulating joint being operatively connected to a distal end of the shaft and configured to move the nozzle along the at least one degree of freedom of movement of the articulating joint; and
- a second mechanical transmission element operatively coupled to the articulating joint and engaged with the end effector so as to move the nozzle corresponding to the at least one degree of freedom of movement of the articulating joint;
- wherein the nozzle is operatively coupled to the first end effector such that, on command of the robotic surgery system, the end effector moves the nozzle while depositing biomaterial to print a tissue engineering construct inside the patient's body, and
- wherein, on command of the robotic surgery system, the end effector moves the nozzle corresponding to the at least one degree of freedom of movement of the articulating joint.

13. The biomaterial delivery system of claim 12, the additive manufacturing device further comprising a tube disposed inside the shaft, the tube configured to transport biomaterial between the reservoir and the nozzle.

* * * * *